(12) United States Patent
Chubb, III et al.

(10) Patent No.: US 8,178,696 B2
(45) Date of Patent: May 15, 2012

(54) PROCESSES FOR PRODUCING N-ALKYLPYRAZOLE

(75) Inventors: John E. Chubb, III, Pennsylvania Furnace, PA (US); John J. Pascavage, Warriors Mark, PA (US)

(73) Assignee: Albemarle Corporation, Baton Rouge, LA (US)

( * ) Notice: Subject to any disclaimer, the term of this patent is extended or adjusted under 35 U.S.C. 154(b) by 0 days.

(21) Appl. No.: 12/937,660

(22) PCT Filed: Apr. 16, 2009

(86) PCT No.: PCT/US2009/040770
§ 371 (c)(1),
(2), (4) Date: Oct. 13, 2010

(87) PCT Pub. No.: WO2009/131886
PCT Pub. Date: Oct. 29, 2009

(65) Prior Publication Data
US 2011/0028734 A1 Feb. 3, 2011

(51) Int. Cl.
*C07D 231/10* (2006.01)

(52) U.S. Cl. ................................................... 548/373.1
(58) Field of Classification Search ............... 548/373.1
See application file for complete search history.

(56) References Cited

U.S. PATENT DOCUMENTS 4,996,327 A   2/1991  Merkle et al.
560,607 A    2/1997  Wroblowsky et al.

FOREIGN PATENT DOCUMENTS

DE     10057194       5/2002
WO     WO 2005/063755  *  7/2005  ................... 544/100

OTHER PUBLICATIONS

Lynch, Brian M. Pyrazolo [3,4-b] pyridines: Syntheses, reactions, and nuclear magnetic resonance spectra. Canadian Journal of Chemistry. 66(3), 1988, 420-428.*

* cited by examiner

*Primary Examiner* — Rebecca Anderson
*Assistant Examiner* — Samantha Shterengarts
(74) *Attorney, Agent, or Firm* — Marcy M. Hoefling; Jeremy J. Kliebert; James A. Jubinsky

(57) ABSTRACT

Processes are provided for combining nonsubstituted hydrazine (N2H4), a strong acid, alcohol, and tetraalkoxypropane to produce N-alkylpyrazole.

4 Claims, No Drawings

PROCESSES FOR PRODUCING N-ALKYLPYRAZOLE

BACKGROUND

This invention relates to processes for producing N-alkylpyrazole. More specifically, but not by way of limitation, the present invention relates to one-pot processes that use nonsubstituted hydrazine as a reactant for producing N-alkylpyrazole.

N-alkylpyrazole, particularly 1-methylpyrazole, is useful in a wide variety of commercial products, including pharmaceutical, electronic, and agricultural products.

Published processes for producing 1-methylpyrazole require the use of methylhydrazine as a reactant. For example, U.S. Pat. Nos. 5,606,074 and 5,569,769 describe processes that use methylhydrazine in order to make 1-methylpyrazole. Methylhydrazine is not readily available in affordable commercial quantities; e.g., many governments purchase significant amounts of available supply for use in military applications, and the cost to purchase methylhydrazine for use in commercial applications can be prohibitive.

In view of the utility of N-methylpyrazole (e.g., 1-methylpyrazole), it would be beneficial to have new commercially suitable processes for producing same.

THE INVENTION

This invention meets the above-described needs by providing process comprising combining at least a strong acid, nonsubstituted hydrazine, $R^1OH$, and

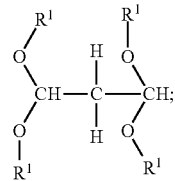

and producing product comprising a plurality of

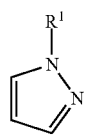

wherein $R^1$ represents $CH_3$, or a primary or secondary alkyl group having from 1 to about 10 carbon atoms. Processes of this invention may further comprise combining at least a portion of the product, $Q^1OH$ and $R^1X^1$, wherein $Q^1$ represents Na or K, and $X^1$ represents chlorine (Cl), bromine (Br) or iodine (I); and producing second product comprising a plurality of

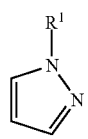

wherein the quantity of

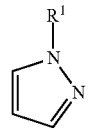

is increased as compared to the product.

$R^1$ can represent $CH_3$ or a primary or secondary alkyl having from 1 to about 10 carbon atoms. For example, $R^1$ can represent ethyl ($C_2H_5$), propyl ($C_3H_7$), butyl ($C_4H_9$), or

wherein each of $R^2$ and $R^3$ independently represents a primary or secondary alkyl having from 1 to about 9 carbon atoms. When $R^1$ represents $CH_3$,

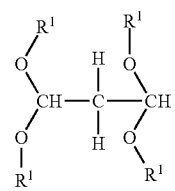

represents tetramethoxypropane, $R^1OH$ represents methanol, $R^1X^1$ represents methylchloride, methylbromide, or methyliodide, and

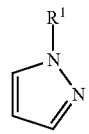

represents N-methypyrazole.

When $Q^1$ represents Na or K, $Q^1OH$ represents sodium or potassium hydroxide.

As used herein, the term "strong acid" means an acid that has a pKa less than about −1.74. Suitable strong acids include, for example, sulfuric acid ($H_2SO_4$), $HX^2$ (where $X^2$ is Cl, Br, or I), and $H_3PO_4$. If desired, an anhydrous, or substantially anhydrous, strong acid may be used. Sulfuric acid is typically commercially available and is easy to use in anhydrous form.

As used herein, the term "nonsubstituted hydrazine" means $N_2H_4$ which may be associated with some amount of water (i.e., $N_2H_4.H_2O$), but in which none of the $H_4$ groups is substituted, e.g., with an alkyl group. As is familiar to those skilled in the art, hydrazine is typically handed in an aqueous solution, e.g., a 60 vol % aqueous solution.

According to this invention, N-methylpyrazole can be formed in a single pot process by reaction of hydrazine sulfate (resulting from combination of nonsubstituted hydrazine and sulfuric acid) and 1,1,3,3-tetramethoxypropane (TMOP) in methanol followed by subsequent methylation with methyl chloride under basic conditions. The following reaction scheme is illustrative of this invention:

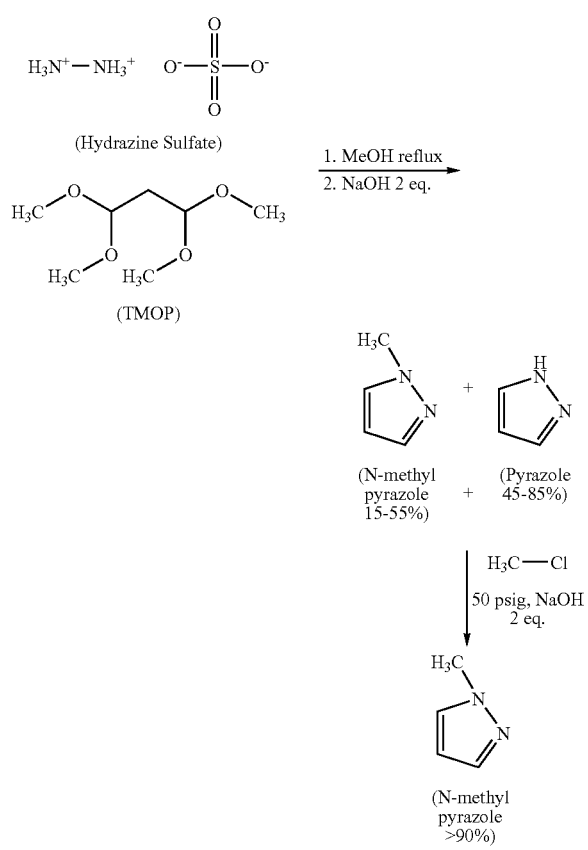

The N-methylpyrazole can be separated from the reaction mixture by fractional distillation at atmospheric pressure as a water-methylpyrazole azeotrope at ca. 50% methylpyrazole. The water can then be removed under Dean-Stark conditions using ethyl acetate; and the final product, substantially anhydrous N-methylpyrazole, can be fractionally distilled to separate it from the ethyl acetate solvent. If pyrazole is a desired product, then the N-methylpyrazole and pyrazole can be separated and isolated without further methylation. Alternatively, the pyrazole can be subsequently methylated with methyl chloride under basic conditions to provide additional N-methylpyrazole. If desired, the methanol can be stripped before addition of the NaOH or other caustic.

EXAMPLE

The following example is illustrative of the principles of this invention. It is understood that this invention is not limited to any one specific embodiment exemplified herein, whether in the examples or the remainder of this patent application.

A 1 L 4-neck roundbottom flask with overhead agitator, thermocouple, and condenser was set up. Hydrazine monohydrate (49.7 g, 0.99 mol) and methanol (140.0 g) were charged to the flask, the flask contents were cooled to 0-10° C., then 96.25% sulfuric acid (98.2 g, 0.96 mol) was slowly charged to the flask with agitation at below 25° C. The reaction was exothermic, and a thick white slurry formed. Cooling was stopped and 1,1,3,3-tetramethoxypropane (158.2 g, 0.99 mol) was charge to the flask. The flask contents were heated to reflux, at 68-69° C., and held for two hours. The thick white slurry transformed to a yellow solution. Gas chromatography showed no remaining tetramethoxypropane, 0.5% methylpyrazole, and 97.4% pyrazole (% is area percent).

The reaction mixture was cooled to 0-10° C., then 50% sodium hydroxide (317.2 g, 3.96 mol) was slowly charged to the reaction mixture at below 25° C. The reaction was exothermic, and solids precipitated, with the color changing to dark green-brown after about ⅓ of the sodium hydroxide charge, or about 105 g, had been added. Cooling was stopped and the reaction mixture was warmed to 50-55° C. for 1 hour, then allowed to cool and held at 20-25° C. for 16 hours. Gas chromatography showed 16.4% methylpyrazole and 82.2% pyrazole.

The reaction mixture was transferred to a pressure reactor, then warmed to 50-55° C.; methyl chloride (92.8 g, 1.83 mol) was charged to the warmed reaction mixture at 30-50 psig over 6 hours. The reactor contents were cooled to 20-25° C., then residual pressure was vented off. Reactor contents were transferred back into the original flask. Gas chromatography showed 93.2% methylpyrazole and 5.6% pyrazole.

The flask was equipped with a distillation column (1 inch×8 inch hastelloy propack) and still head. Methanol was fractionally distilled at atmospheric pressure to 98° C. pot and 69° C. head temperatures. Water (103.6 g) was charged to the flask. The flask at this point had solids and two liquid layers present. Fractional distillation was continued to 99° C. pot and 75° C. head temperatures to remove methanol (217.0 g). A forerun fraction was taken to 90° C. head (2.7 g, 8.6 wt % methylpyrazole), then a methyl pyrazole/water azeotrope fraction was taken at 97-98° C. head (142.6 g, 38.5 wt % methylpyrazole, 52.8% water). The reaction mass remaining in the flask was cooled and water (378.6 g) was charged to the flask to dissolve salts prior to disposal.

Ethyl acetate (167.5 g) and the methylpyrazole/water azeotrope fraction were charged to the flask and the flask was equipped with the distillation column and a Dean-Stark head. The flask contents were refluxed, using the Dean-Stark head to selectively remove the water fraction of the distillate (86 g), until water was no longer observed in the distillate. The Dean-Stark head was replaced with a still head and the contents were fractionally distilled under atmospheric pressure to 125° C. pot and 78° C. head to remove ethyl acetate (95.7, 0.1 wt % methylpyrazole). A forerun fraction was taken to 124° C. head (7.2 g, 8.0 wt % methylpyrazole), then a product fraction was taken at 127° C. (51.2 g, 99.5% methylpyrazole, 0.62 mol). The pot heel (8.3 g, 98.4% methyl pyrazole, 0.10 mol) was available, e.g., for recycle.

Processes according to this invention are commercially advantageous compared to processes that require the use of methylhydrazine as a reactant given that hydrazine (nonsubstituted) costs about $2.17/lb compared to about $90.00/lb for methylhydrazine.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

What is claimed is:

1. A process comprising:
   combining at least a strong acid, nonsubstituted hydrazine, methanol, and tetramethoxypropane; and
   producing one or more

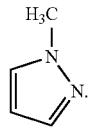

2. The process of claim 1 in which the strong acid is sulfuric acid.

3. The process of claim 1 further comprising:
   combining (i) one or more of the produced

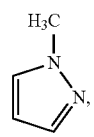
(ii)

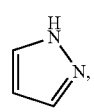
(iii)

sodium or potassium hydroxide, and (iv) methylchloride, methyliodide, or methylbromide; and
   producing additional

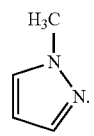

4. The process of claim 3 in which the strong acid is sulfuric acid.

* * * * *